US006496558B2

(12) United States Patent
Graumann

(10) Patent No.: US 6,496,558 B2
(45) Date of Patent: Dec. 17, 2002

(54) X-RAY DEVICE AND MEDICAL WORKPLACE FOR DIAGNOSTICS AND SURGICAL INTERVENTIONS IN THE HEAD AND/OR JAW OF A PATIENT

(75) Inventor: Rainer Graumann, Hoechstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/792,120

(22) Filed: Feb. 22, 2001

(65) Prior Publication Data

US 2001/0036246 A1 Nov. 1, 2001

(30) Foreign Application Priority Data

Feb. 22, 2000 (DE) .......................................... 100 08 053

(51) Int. Cl.⁷ ................................................. A61B 6/14
(52) U.S. Cl. .......................................... 378/39; 378/197
(58) Field of Search ............................... 378/4, 19, 38, 378/39, 195, 196, 197, 205

(56) References Cited

U.S. PATENT DOCUMENTS

| 5,012,501 | A |   | 4/1991  | Palonen et al. |           |
|-----------|---|---|---------|----------------|-----------|
| 5,253,171 | A |   | 10/1993 | Hsiao et al.   |           |
| 5,287,274 | A | * | 2/1994  | Saint Felix et al. | 378/13 |
| 5,666,392 | A |   | 9/1997  | Ploetz         |           |
| 6,050,724 | A |   | 4/2000  | Schmitz et al. |           |
| 6,118,842 | A |   | 9/2000  | Arai et al.    |           |
| 6,120,180 | A |   | 9/2000  | Graumann       |           |
| 6,155,713 | A | * | 12/2000 | Watanabe       | 378/197   |
| 6,200,024 | B1| * | 3/2001  | Negrelli       | 378/196   |
| 6,317,621 | B1| * | 11/2001 | Graumann et al.| 378/62    |

FOREIGN PATENT DOCUMENTS

| DE | 196 36 354  | 3/1996  |
|----|-------------|---------|
| EP | 0 641 545   | 9/1994  |
| WO | WO 97/40766 | 11/1997 |

* cited by examiner

Primary Examiner—David P. Porta
(74) Attorney, Agent, or Firm—Schiff Hardin & Waite

(57) ABSTRACT

In an X-ray device and workplace for obtaining radiological exposures of the head and jaw region of a patient an X-ray source emits a conical X-ray bundle which is detected at and an X-ray detector to acquire a 3D dataset of the head or jaw region of the patient. The workplace also can include a navigation system.

7 Claims, 4 Drawing Sheets

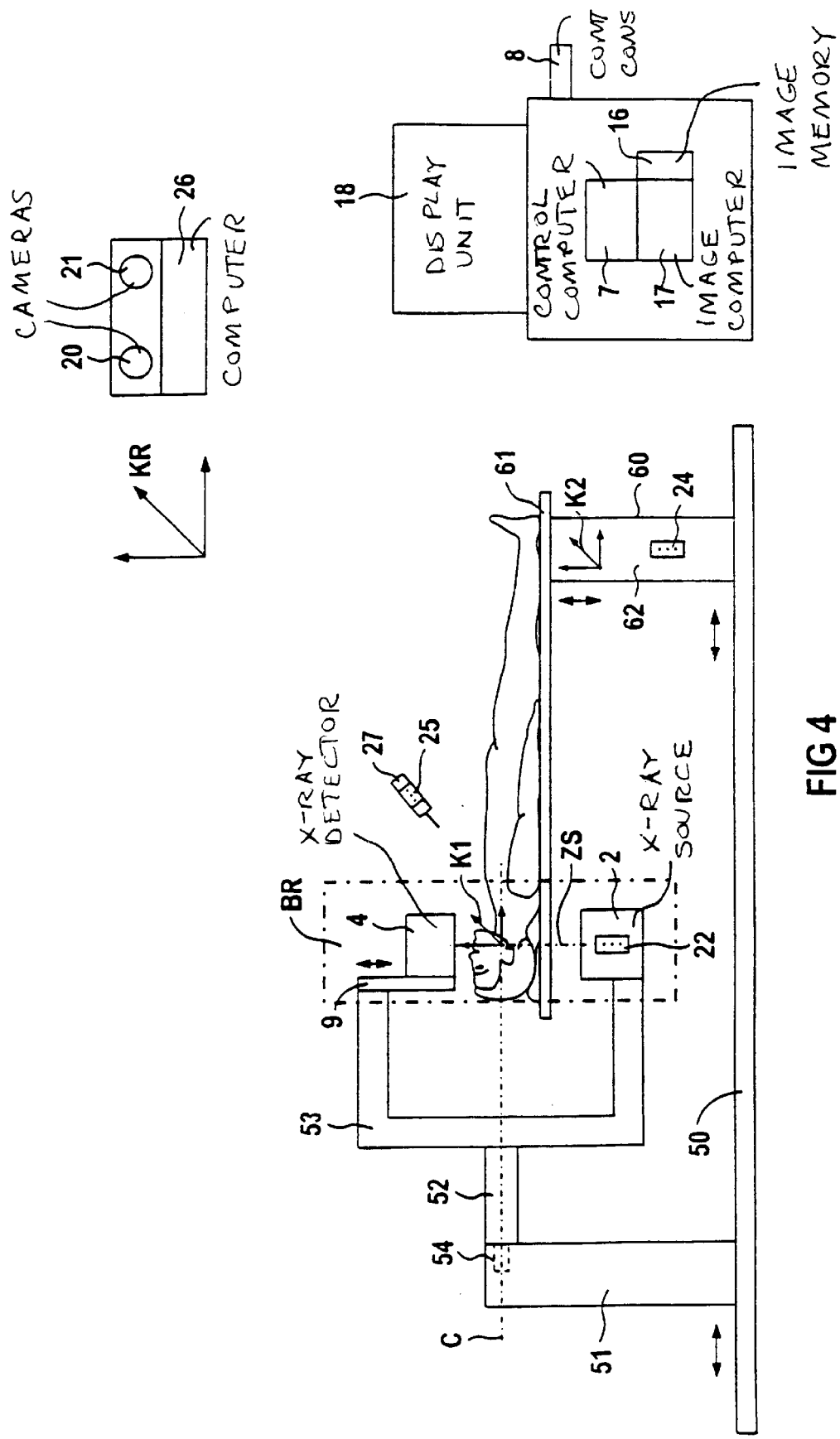

X-RAY DEVICE AND MEDICAL WORKPLACE FOR DIAGNOSTICS AND SURGICAL INTERVENTIONS IN THE HEAD AND/OR JAW OF A PATIENT

BACKGROUND OF THE INVENTION

1. Field of the Invention

The present invention relates to an X-ray device for obtaining radiological exposures of the head and jaw region of a patient, of the type having an X-ray source and an X-ray detector for picking up 2D projections of the head or jaw region of the patient. The invention also relates to a medical workplace for diagnostics and for surgical interventions in the mouth, jaw or face region of a patient, employing such an X-ray device.

2. Description of the Prior Art

Radiological exposures of the jaw, X-ray projection exposures of individual teeth, X-ray panorama exposures of the jaw or computer tomography exposures for acquiring 3D images of tissue areas of the head or of the jaw are carried out for diagnosis and for planning dental surgical interventions, tooth implants or interventions in the facial region of a patient. For financial reasons, the latter are only prepared in justified individual cases, for example for planning tooth implants or reconstructive interventions in the face/skull region, for which intervention planning on the basis of 3D images is indispensable. An X-ray computed tomography apparatus is a relatively expensive image pickup device, and only very few dental surgeons have such a device, so the planning and implementation of a dental surgical intervention normally requires a number of process steps, which do not follow immediately after one another and which may not all be performable by the dental surgeon. For planning and implementing a tooth implantation, the following is necessary, for example:

a) preparing overview exposures of the jaw at the dental surgeon, b) if needed, obtain images of the jaw done with an X-ray computed tomography apparatus at a radiologist, c) transferring the computed tomography data to the dental surgeon, d) planning the intervention at the dental surgeon e) performing the intervention on the patient.

For example, German OS 40 12 627, corresponding to U.S. Pat. No. 5,012,501, describes an X-ray device for picking up panoramic X-ray images of a jaw on X-ray film.

German OS 196 36 354 discloses a device for obtaining optical images of a tooth, in particular.

SUMMARY OF THE INVENTION

An object of the present invention is to provide an X-ray device, and a workplace provided with such an X-ray device, which can be economically produced and with which 3D images of the head and jaw region of a patient can be acquired in a relatively inexpensive manner.

This object is inventively achieved in an X-ray device for obtaining radiological exposures in the head and jaw region of a patient, having an X-ray source and an X-ray detector, which can be arranged or are arranged opposite each another such that the central beam of a conical X-ray bundle originating from the X-ray source strikes the X-ray detector approximately centrally, and having an arrangement for moving the X-ray source and the X-ray detector, by motor-adjustment, around an axis for picking up a series of 2D projections of the head or jaw region of the patient, and having a computer for generating a 3D image dataset from the acquired 2D projections. Similar to rotation angiography devices or adjustable C-arm X-ray devices, the inventive X-ray device has an X-ray source which emits a conical X-ray bundle. The X-ray source can be displaced around an axis of the X-ray device together with the X-ray detector. The head of the patient to be examined is normally supported along this axis. During the adjustment motion around the axis, a series of 2D projections is acquired from different projection angles of the head or jaw region of the patient, so that a 3D image dataset can be acquired from the head or jaw region of the patient. The structure of the X-ray device, for example the distance of the X-ray source from the X-ray detector and the adjustment range of the X-ray source and of the X-ray detector, is adapted to the requirements in the mouth, jaw and face region of the patient. The X-ray device therefore can be kept relatively small. The distance between the X-ray source and the X-ray detector preferably is one meter at a maximum. Since relatively economic and proven components can be used in the inventive X-ray device, the X-ray device can be relatively inexpensively produced. Therefore, the cost for equipping a dental surgical office with such an X-ray device is reasonable affordable, so that a dental surgeon, without time delays due to multiple sessions, can carry out the image pickup, the intervention planning, and the intervention at the patient in steps that directly follow one another.

In a version of the invention, the arrangement for adjusting (positioning) the X-ray source and the X-ray detector has two supports to which the X-ray source and the X-ray detector are respectively mounted, which can be motor-adjusted around the axis of the X-ray device and which can be motor-adjusted relative to one another. Such supports can be guided at a track that runs circularly around the axis and that is mounted to the ceiling, for example. In another version of the invention the X-ray source and the X-ray detector are arranged at a carrier fashioned in a U-shaped or C-arm-shaped manner, and the carrier is rotated by a motor-drive around the aforementioned axis which proceeding extends through the carrier. The carrier can be arranged around a vertically proceeding axis when mounted to the ceiling or can be rotated around a horizontally proceeding axis when arranged at a holding device.

In a particularly preferred embodiment of the invention, the motor-adjustment of the supports, or the motorized rotation of the carrier, is effected by at least one digitally controlled drive. The drive is preferably software-controlled, and can be a stepper motor in an embodiment of the invention. This allows precise adjustment of the support relative to one another, or precise rotation of the carrier device, so that different positions of the support or carrier can be repeatedly reached with high exactness. Since the X-ray device can be kept relatively small overall, the structure of the X-ray device exhibits a high rigidity, so that the adjustment movements of the X-ray system can be accurately reproduced.

In a further version of the invention the X-ray detector can be adjusted relative to its support, or relative to the carrier, in the direction of the central beam. In this way, the X-ray detector can be placed relatively close to the head of the patient and the size of the image field therefore can be optimally adjusted for the respective examination case. The X-ray source and the X-ray detector therefore normally move asymmetrically around the axis or the head of the patient during the pickup of a series of 2D projections.

The above object also is achieved in a medical workplace for diagnostics and for surgical interventions in the mouth, jaw, or face area of a patient, having an X-ray device as described above, a patient support and an arrangement for determining the positions of the X-ray device and the patient support relative to one another, and wherein the X-ray device and the patient support are arranged relative to one another in a defined way and can be mechanically adjusted relative to one another in a defined way.

The object also is achieved in a medical workplace for diagnostics and for surgical interventions in the mouth, jaw, or face area of a patient, having an X-ray device, as described above, a patient support and a navigation system for determining the positions of the X-ray device and the patient support relative to one another.

Both embodiments of the medical workplace make it possible for the dental surgeon to simply and conveniently transfer the planning results obtained on the basis of the 3D image data immediately to the patient and to carry out the intervention as a result of the knowledge of the spatial relationship between the X-ray device, and therefore the 3D image dataset generated by the X-ray device, and the patient on which the patient is borne, and normally fixed. Given adjustments of the patient support relative to the X-ray device, and therefore relative to the 3D image dataset, the representation of generated 3D images can be automatically adapted to the modified position of the patient in the course of the intervention as a result of the known spatial relationship between the 3D image dataset and the patient support.

In a version of the invention, a navigation system not only determines the position of the X-ray device and/or of the patient support but also determines the position of at least one instrument used during a dental-surgical intervention, so that the imaging of the instrument into an image acquired by the X-ray device is enabled for supporting the surgical intervention. In this way, the surgeon can navigate an instrument introduced into the body of the patient on the basis of the image information displayed at a display unit, so that an expedient support of the surgical intervention is assured.

DESCRIPTION OF THE DRAWINGS

FIG. 4 shows a dental-surgical workplace with an X-ray system in accordance with the invention, in an embodiment having arranged at a U-shaped carrier.

DESCRIPTION OF THE PREFERRED EMBODIMENTS

Figure 1:
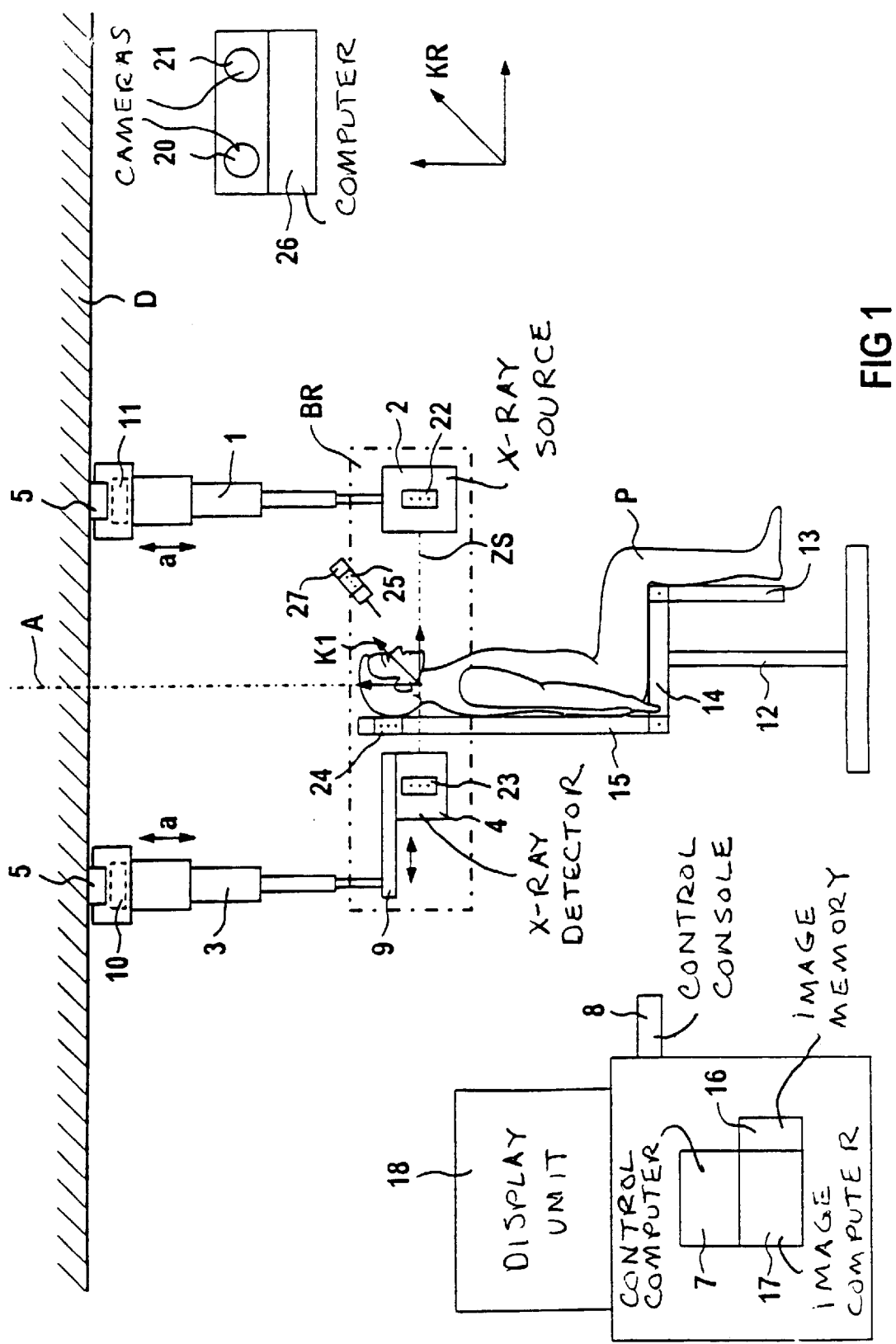
FIG. 1 shows a dental-surgical workplace with an X-ray system in accordance with the invention, in an embodiment having two supports that are arranged in a track at a ceiling, and with a navigation system.

FIG. 1 shows an inventive medical workplace for diagnostics and for surgical interventions in the mouth, jaw, or face area of a patient P. The workplace has an X-ray device for radiological exposures of the head and jaw region of the patient P, a patient support, and a navigation system.

The X-ray device includes an X-ray source 2 arranged at a support 1 and an X-ray detector 4 arranged at a support 3. The X-ray detector 4 can be an X-ray image intensifier or an aSi-flat panel image detector, for example. The X-ray source 2 and the X-ray detector 4 are respectively arranged at the supports 1 and 3 such that a central beam ZS of a conical X-ray bundle proceeding from the X-ray source 2 strikes the input screen of the X-ray detector 4 approximately centrally.

The supports 1 and 3 are basically identically fashioned and are arranged in a track 5 at the ceiling. In the exemplary embodiment, the supports 1 and 3 are telescopic supports, which can be vertically adjusted in the directions of the double arrows a by electrical drives (not shown). In this way, the X-ray source 2 and the X-ray detector 4, for radiological exposures, can be brought into a medical treatment room BR (indicated by broken lines in FIG. 1) or can be brought out of the medical treatment room BR. The adjustment of the supports 1, 3 is controlled by a control computer and is preferably synchronized, so that the X-ray source 2 and the X-ray detector 4 always remain relatively oriented to one another. The supports 1, 3 can be vertically adjusted at a control console 8 by an operator. In contrast to the arrangement of the X-ray source 2 at the stand 1, the X-ray detector 4 is arranged at a adjustment device 9 attached to the support 3 such that it can be adjusted in the direction of the central beam ZS of the X-ray bundle in a geometrically determined way. The size of the image field can thus be adapted to the respective exposure situation during the acquisition of 2D projections.

Figure 2:
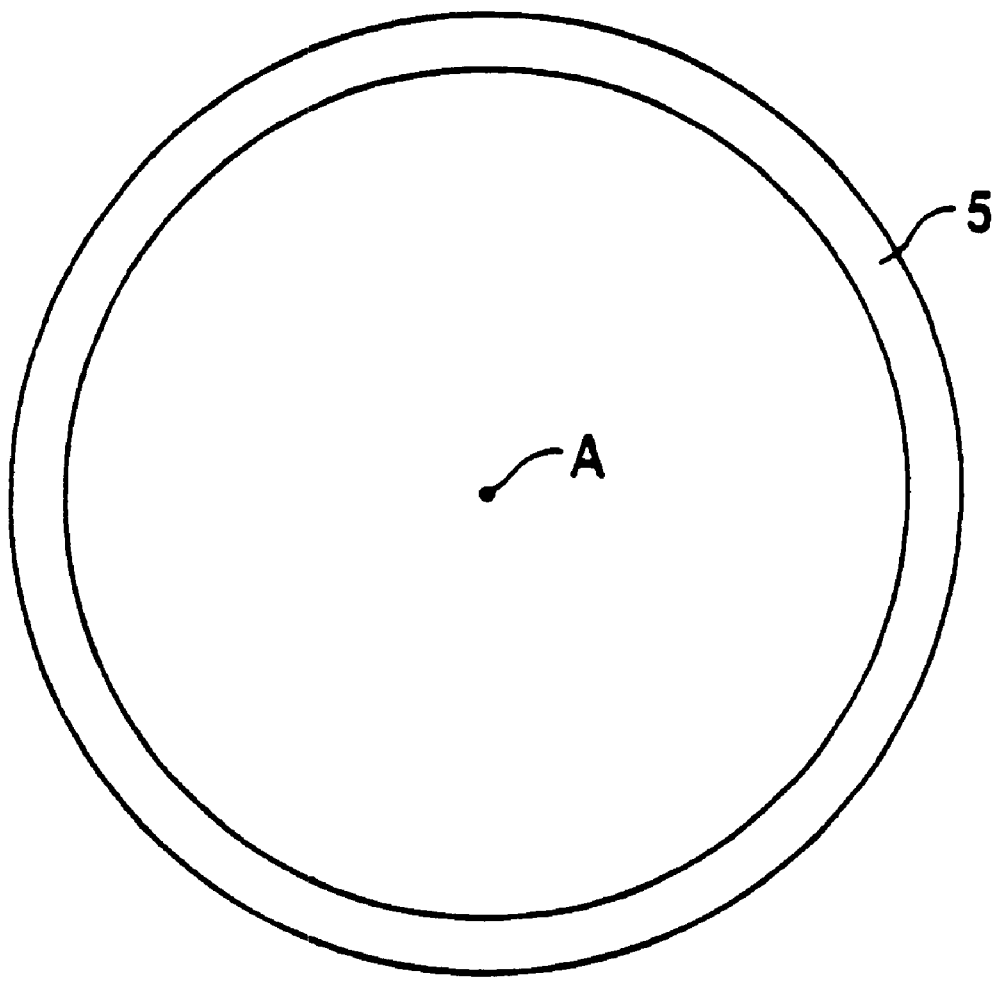
FIG. 2 shows the curve of the track at the ceiling (from FIG. 1).

The supports 1 and 3 can be adjusted in the track 5 by software-controlled, digital electrical drives in the form of two stepper motors 10 and 11, so that the supports 1, 3 move circularly around a vertical axis A of the X-ray system. FIG. 2 schematically shows the track 5, proceeds circularly around the axis A and which is mounted to the ceiling D. The control computer 7 controls the adjustment of the supports 1, 3 in the track 5 such that the X-ray source 2 and the X-ray detector 4 are synchronously adjusted imposition and such that the X-ray source 2 and the X-ray detector 4 remain relatively oriented to one another.

The patient P is borne on a patient support in the form of a patient chair 12. In the present exemplary embodiment, the patient chair 12 is fashioned such that its elements 13, 14 and 15 can be adjusted by motors relative to one another in a known manner. The patient P therefore can be placed into different positions relative to the X-ray device. Preferably, the patient P is fixed on the patient chair 12, so that he or she cannot change position on the patient chair 12 during the treatment.

For acquiring a series of 2D projections of the head or jaw region of the patient P, the supports 1, 3, controlled by the control computer 7 with the stepper motors 10, 11, are synchronously displaced around the axis A. The X-ray detector 4 is thereby normally asymmetrically adjusted relative to the X-ray source 2. The 2D projections acquired at different projection angles during the adjustment of the X-ray system are temporarily stored into an image memory 16 of the X-ray device and are made available to an image computer 17 for generating a 3D image dataset. The image computer 17 receives the projection geometries, which are necessary for generating a 3D image dataset, directly from the control computer 7. The projection geometries are the positions of the X-ray source 2 and of the X-ray detector 4, as well as the projection angles for the different 2D projections in the arbitrarily selectable X-ray coordinate system K1. The control computer 7 calculates the position data of the X-ray source 2 and the X-ray detector 4, which are arranged at the supports 1, 3 and around the axis A in a geometrically defined (known) way, from the control data of the step motors 10, 11. The initial position of the X-ray source 2 and of the X-ray detector 4 are known to the control computer 7 from the control data of the electrical drive effecting the vertical adjustment of the telescopic supports 1, 3, from the control data of the stepper motors 10, 11 and from the adjustment data of the adjustment device 9. The image computer 17 can generate various 3D images of the head or jaw region of the patient P from the 3D dataset in a known manner and the images are shown at a display 18.

On the basis of the 3D images of the head or jaw region of the patient P, a dental surgeon (not shown in FIG. 1) can plan the upcoming intervention at the patient immediately following the image pickup. It is advantageous that the positions of the generated 3D image dataset, and the 3D images generated therefrom, are also known in the X-ray coordinate system K1 on the basis of the known positions of the X-ray source 2 and the X-ray detector 4 during the pickup of the 2D projections. In this way, the dental surgeon can directly transfer the results of the planning to the patient P and can immediately carry out the intervention at the patient P. For example, such a planning is composed of the determination of the location and the orientation of a boring, which is provided for accepting a pivot for a tooth implant. On the basis of a 3D image, the physician can determine the data required for the boring and can subsequently perform the boring at the jaw of the patient P.

In the exemplary embodiment, the spatial relationship between the X-ray device, the patient chair 12 on which the patient P is fixed, and a dental-surgical instrument 27 is acquired with the aid of a navigation system in order to be able to correspondingly adapt the imaging during adjustments of the patient chair 12 relative to the X-ray device and in order to be able to mix a representation of the instrument 27 into a 3D image and navigate it relative to the patient P.

In the exemplary embodiment, the navigation system for determining the spatial relationship between the X-ray device, the instrument 27 and the patient chair 12 and therefore the patient P situated on the patient chair 12 is an optical navigation system comprising cameras 20, 21 and optical reference elements 22 to 25, which, in a defined way, are arranged at the objects to be acquired concerning their position and which are picked up by the cameras 14, 15. A computer 26 of the navigation system evaluates the images picked up by the cameras 20, 21 and, on the basis of the picked up reference elements 22 to 25, can determine the positions, i.e., the orientations of the reference elements 22 to 25 and therefore of the corresponding objects in an arbitrarily selectable reference coordinate system KR.

In the present exemplary embodiment, the reference element 22 is arranged at the X-ray source 2, the reference element 23 is arranged at the X-ray detector 4, the reference element 24 is arranged at the element 15 of the patient chair 12 and the reference element 25 is arranged at the instrument 27 to be guided by the dental surgeon. On the basis of the acquired camera images, the computer 26 can determine the current respective positions of the X-ray source 2, the X-ray detector 4, the element 15 and the instrument 27 in the reference coordinate system KR. The computer 26, which is connected to the image computer 17 in a way that is not shown, respectively provides the image computer 17 with the data about the current positions of the X-ray source 2, the X-ray detector 4, the element 15, of the patient chair 12, and the instrument 27. In this way, the image computer 17 can create a relationship between the X-ray coordinate system K1 and the reference coordinate system KR and can determine the coordinates of the 3D image dataset with respect to the reference coordinate system KR. Given a modification of the position of the patient chair 12 and therefore of the head of the patient P, it is thus possible to adjust the 3D image dataset to the new position of the head of the patient P and it is also possible to correspondingly adapt the image representation at the display 18. If the element 15 of the patient chair 12 is adjusted, for example, in the course of the treatment of the patient P relative to the element 14, so that a modification of the position of the head of the patient results, the navigation system registers this and the image computer 17 can optimally adapt the modified position of the head of the patient P to the image representation.

With the navigation system, it is also possible to mix an image of the instrument 27 into a 3D image of the head or jaw region of the patient P acquired with the X-ray device as a result of the determination of the position of the instrument 27 relative to the patient chair 12, and therefore relative to the patient P and the 3D image dataset in the reference coordinate system KR, and to support the surgical intervention in this way. This is particularly advantageous when, for example, the tip of the instrument 27 is no longer visible during the operation as a result of the introduction into the jaw region of the patient P.

Figure 3:
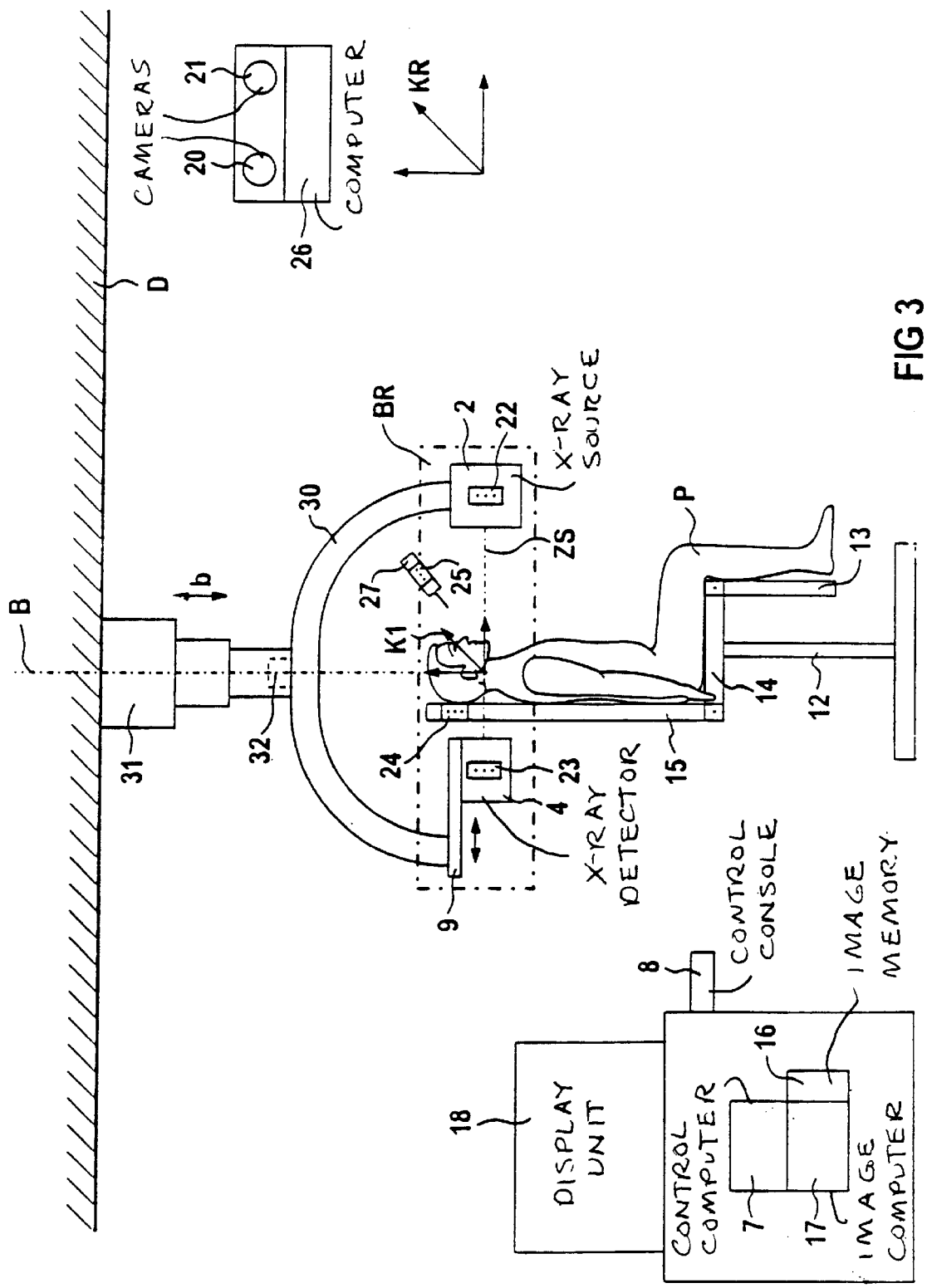
FIG. 3 shows a dental-surgical workplace with an X-ray system in accordance with the invention, in an embodiment having arranged at a C-arm at the ceiling, and with a navigation system.

FIG. 3 shows a second, inventively fashioned medical workplace for diagnostics and for surgical interventions in the mouth, jaw or face area of the patient P. The medical workplace shown in FIG. 3 exhibits the same functions and has the same construction as the previously described workplace shown in FIG. 1. In contrast to the medical workplace shown in FIG. 1, the X-ray device of the medical workplace shown in FIG. 3 has a C-arm 30, which is mounted to the ceiling and which can be rotated around a vertical axis B. The X-ray source 2 and an X-ray detector 4, which are opposite to one another, are arranged at the C-arm 30 in a defined way. The central beam ZS of a conical X-ray bundle proceeding from the X-ray source 2 strikes the input screen of the X-ray detector 4 approximately centrally. The X-ray detector 4 is arranged at the C-arm 30 via the adjustment device 9 such that it can be displaced in a geometrically defined way in the direction of the central beam ZS. The C-arm 30 is attached to the ceiling D of the medical treatment room via a telescopic-like holding device 31 and can be vertically displaced in the directions of the double arrow b by electrical drives (not shown) that are driven by the control computer 7. The C-arm 30 can be rotated around the axis B relative to the holding device 31 by a stepper motor 32, which is also driven by the control computer 7.

For acquiring a 3D image dataset of the head or jaw region of the patient P, the C-arm 30, driven by the stepper motor 12, is rotated around the axis B, whereby a series of 2D projections are picked up at different projection angles. The image computer 17 subsequently uses the 2D projections, which are temporarily stored in the image computer 16, together with the projection geometries provided by the control computer 7 (as in the case of the exemplary embodiment described in FIG. 1) for generating a 3D image dataset of the head or jaw region of the patient P. The control computer 7 thereby determines the projection geometries from the control data of the step motor 32, whereby the initial position of the X-ray system is known to the control computer 7 from the control data of the electrical drives of the holding device 31 and from the adjustment data of the adjustment device 9. The position of the 3D image dataset in the X-ray coordinate system K1 is also known due to the known positions of the X-ray system during the pickup of the 2D projections, so that it is possible to directly transfer planning results acquired on the basis of 3D images to the patient P.

As described before, a relationship between the X-ray coordinate system K1 and the reference coordinate system KR can be created with the aid of the navigation system, so that the position of the 3D image dataset, when the patient chair 12 is adjusted, can be adjusted to the head of the patient P and the instrument 27 can be navigated.

FIG. 4 shows a third exemplary embodiment of an inventive medical workplace having an X-ray device and a patient support. Components of the workplace having essentially the same construction and functions as components of the workplace shown in FIG. 1 are provided with the same reference numbers.

The X-ray device has a stand column 51, which can be adjusted in a track 50 in a motorized manner and which has a holding device 52 for accepting an U-shaped carrier 53. The X-ray source 2 and the X-ray detector 4 are oppositely arranged at the U-shaped carrier 53 in a defined way such that a central beam ZS of a conical X-ray bundle originating from the X-ray source 2 strikes the input screen of the X-ray detector 4 approximately centrally. As in the previously described exemplary embodiments, the X-ray detector 4 is arranged at the adjustment device 9 and can be adjusted therewith in a defined way in the direction of the central beam ZS. The holding device 52 of the U-shaped carrier 53, together with the carrier 53, can be rotated relative to the support column 51 around an axis C, which proceeds substantially horizontally through the U-shaped carrier 53 and which is referred to as the angulation axis.

In the exemplary embodiment shown in FIG. 4, the patient P is borne on a patient bed 60 having a patient support plate 61 and a telescopic column 62. The telescopic column 62 (in a way that is not shown) is also adjustable by motor in the track 50. The control computer 7 controls the vertical motorized adjustment of the support column 51 and the telescopic column 62 in the track 50. The control computer 7 therefore knows the positions of the X-ray device and of the patient bed 60 relative to one another.

For acquiring a 3D image dataset of the head or jaw region of the patient P, the carrier device 53, which is moved by a stepper motor 54 driven by the control computer 7, is rotated around the axis C, whereby a series of 2D projections is picked up at different projection angles. Together with the projection geometries, which are provided by the control computer 7 and which are acquired from the control data of the step motor 54 (as in the exemplary embodiments shown in FIGS. 1 and 3), the image computer 17 subsequently uses the 2D projections that are temporarily stored into the image memory 16 for generating a 3D image dataset of the head or jaw region of the patient P. The position of the 3D image dataset in the X-ray coordinate system K1 is known again due to the known positions of the X-ray system during the pickup of the 2D projections. It is therefore possible to directly transfer the planning results acquired on the basis of 3D images to the patient P.

Since the track-based system of the adjustment of the X-ray device and the patient support device is a precise mechanical adjustment system, wherein the position data of the X-ray device and the patient support device are known to the control computer 7, the image computer 17, on the basis of the position data of the control computer 7, can create a relationship between the arbitrarily selectable coordinate system K1 of the X-ray device and an arbitrarily selectable coordinate system K2 of the patient support even without the navigation system. In this way, the image computer 17 can adjust the 3D image dataset to the position of the head of the patient P and the image representation can be possibly adapted given a modification of the position of the patient P as a result of adjustment movements of the patient bed 60.

The navigation system (previously described and shown in FIGS. 1 and 3) can be additionally present at the medical workplace in order to be able to mix images of the instrument 27 into 3D images of the mouth or jaw region of the patient P that are generated by the X-ray device. Since the control computer 7 knows the positions of the X-ray device and of the patient bearing device relative to one another due to the mechanical adjustment system, it is sufficient to only provide the X-ray device or the patient support device with a reference element 22 or 24, respectively, in order to determine the positions of the X-ray device and the patient support device in the reference coordinate system KR and in order to be able to navigate the instrument 27. The computer 26 and the control computer 7 provide the image computer 17 with the position data necessary for this purpose, so that it can mix images of the instrument 27 into 3D images acquired from the 3D image dataset in a true-to-reality manner.

The previously described navigation system need not necessarily be an optical navigation system. Mechanical, acoustic or electromagnetic navigation systems can be utilized as well.

The FIGS. 1–4 do not show the electrical connections between the components of the respective workplaces, for example the connections between the stepper motors and the control computer 7 or between the computer 26 and the image computer 17, since they are fashioned in a known way.

Mixtures of the exemplary embodiments shown in the FIGS. 1 to 4 are possible.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray device for obtaining radiological exposures of the head and jaw region of a patient, comprising:
   an X-ray source which emits a conical X-ray bundle, having a central beam;
   a radiation detector disposed relative to said X-ray source so that said central beam strikes said detector approximately centrally;
   a supporting arrangement for said X-ray source and said radiation detector, said supporting arrangement comprises a first support stand on which said X-ray source is mounted and a second support stand on which said radiation detector is mounted;
   a motorized drive for rotating said supporting arrangement around an axis for picking up a series of 2D projections of a patient region selected from the group consisting of the head region and the jaw region; and
   a computer supplied with said 2D projections for generating a 3D image dataset therefrom.

2. An X-ray device as claimed in claim 1 wherein said motorized drive includes at least one digitally controlled drive.

3. An X-ray device as claimed in claim 2 wherein said digitally controlled drive is a stepper motor.

4. An X-ray device as claimed in claim 1 wherein said radiation detector is mounted for adjustment along a direction of said central beam.

5. A medical workplace for diagnostics and surgical interventions in a head or jaw region of a patient, comprising:
   an x-ray source which emits a conical X-ray bundle having a central beam;

a radiation detector disposed relative to said X-ray source so that said central beam strikes said detector approximately centrally;

a patient support adapted to receive a patient to orient the patient's head between said X-ray source and said radiation detector;

a supporting arrangement for supporting said X-ray source and said radiation detector;

a motorized drive for rotating said supporting arrangement around an axis to obtain a series of 2D projections of the head region of the patient;

a position identifying arrangement for obtaining position information, at least while said series of 2D projections are obtained, identifying respective positions of said X-ray source, said radiation detector and said patient support; and a computer supplied with said series of 2D projections and said position information for generating a 3D image dataset from said series of 2D projections and said position information.

6. A medical workplace as claimed in claim 5 wherein said position identification arrangement is a navigation system.

7. A medical workplace as claimed in claim 5 further comprising an instrument adapted for use in a surgical intervention at the head of the patient, and wherein said position identification system also identifies a position of said instrument, and further comprising a display connected to said computer at which an image produced from said 3D image dataset is displayed, showing a position of said instrument within said image.

* * * * *